US00PP17257P2

(12) United States Plant Patent
Tristam

(10) Patent No.: US PP17,257 P2
(45) Date of Patent: Dec. 5, 2006

(54) ***EUPHORBIA* PLANT NAMED 'WALEUPHRUD'**

(50) Latin Name: *Euphorbia×martinii*
Varietal Denomination: WALEUPHRUD

(76) Inventor: David Tristam, Walberton Nursery, Yapton Lane, Walberton, Arundel (GB), BN18 OAS ( * ) Notice: Subject to any disclaimer, the term of this patent is extended or adjusted under 35 U.S.C. 154(b) by 16 days.

(21) Appl. No.: 11/235,772

(22) Filed: Sep. 26, 2005

(51) Int. Cl.
*A01H 5/00* (2006.01)

(52) U.S. Cl. ..... Plt./302

(58) Field of Classification Search ..... Plt./302
See application file for complete search history.

*Primary Examiner*—Kent Bell
*Assistant Examiner*—June Hwu

(57) ABSTRACT

A new cultivar of *Euphorbia* named 'WALEUPHRUD' that is distinguishable by compact habit, grey-green leaves, shoots of bright red winter bract-leaves, and yellow-green flowers with red centers. In combination these traits set 'WALEUPHRUD' apart from all other existing varieties of *Euphorbia* known to the inventor.

3 Drawing Sheets

Genus: *Euphorbia*. Species:×*martinii*.
Denomination: WALEUPHRUD.

BACKGROUND OF THE INVENTION

The present invention relates to a new and distinct cultivar of spurge, an ornamental plant that is grown for use in container, rock garden, and as a groundcover in the landscape. The new invention is known botanically as *Euphorbia×martinii*, and will be referred to hereinafter by the cultivar name 'WALEUPHRUD'.

In 2000 'WALEUPHRUD' was selected by the inventor, in a cultivated area of Walberton, West Sussex, United Kingdom. Selection was based on the unique criterion that shoots of bright red bract-leaves are produced in winter. 'WALEUPHRUD' was discovered at the inventor's nursery as a naturally occurring single branch sport, on an individual *Euphorbia×martinii*, that was growing in a commercial crop of *Euphorbia×martinii*. The parent is an individual *Euphorbia×martinii* (unpatented). The parent is widely available in commerce and the closest known plant to the inventor. 'WALEUPHRUD' is distinguishable from the parent by shoots of bright red bract-leaves that are produced in winter.

The new *Euphorbia* variety named 'WALEUPHRUD' exhibits compact habit, grey-green leaves, bright red apical shoots in winter, and yellow-green flowers with red centers. Asexual propagation is accomplished by the method of vegetation cuttings. Blooming occurs in spring and summer, and 'WALEUPHRUD' achieves a height of approximately 60 cm and a width of 60 cm at maturity.

The first asexual reproduction of 'WALEUPHRUD' was conducted in 2001 by the inventor in a cultivated area of West Sussex within the United Kingdom. The method used for asexual propagation was vegetative cuttings. Since then the characteristics of the new *Euphorbia* cultivar named 'WALEUPHRUD' have been determined stable, firmly fixed, and 'WALEUPHRED' reproduces true to type in successive generations of asexual propagation.

SUMMARY OF THE INVENTION

The following traits have been repeatedly observed and represent the distinguishing characteristics of the new *Euphorbia* cultivar named 'WALEUPHRUD'. These traits in combination distinguish 'WALEUPHRUD' from all other existing varieties of *Euphorbia* known to the inventor. 'WALEUPHRUD' has not been tested under all possible conditions and phenotypic differences may be observed with variations in environmental, climatic, and cultural conditions, however, without any variance in genotye.

1. *Euphorbia×martinii* 'WALEUPHRUD' exhibits compact habit.
2. In winter the young apical foliage of *Euphorbia×martinii* 'WALEUPHRUD' turns red.
3. *Euphorbia×martinii* 'WALEUPHRUD' produces yellow-green flowers with red centers, in spring and summer.
4. *Euphorbia×martinii* 'WALEUPHRUD' exhibits green and red stems.
5. *Euphorbia×martinii* 'WALEUPHRUD' is asexually propagated using the method of vegative cuttings.
6. *Euphorbia×martinii* 'WALEUPHRUD' is hardy from USDA Zone 7 to USDA Zone 10.
7. *Euphorbia×martinii* 'WALEUPHRUD' achieves approximately 60 cm. in height and 60 cm. in width at maturity.
8. *Euphorbia×martinii* 'WALEUPHRUD' is grown for use in container, rock garden, and as a groundcover in the landscape.

BRIEF DESCRIPTION OF THE DRAWINGS

The accompanying color drawings

FIG. 1 depicts an individual whole container plant from a side perspective and was taken in spring immediately prior to emergence of the bracts (inflorescence).

FIG. 2 depicts a close-up view of the young apical foliage and flowers in winter.

FIG. 3 depicts shoots of bright red bract-leaves in winter.

FIG. 1, FIG. 2, and FIG. 3 were made in United Kingdom using 12–15-month-old plants in 1-liter containers. The drawings were made using conventional techniques and although flower and foliage color may appear different from actual colors due to light reflectance, they are as accurate as possible by conventional photography.

BOTANICAL DESCRIPTION OF THE PLANT

Figure 1:
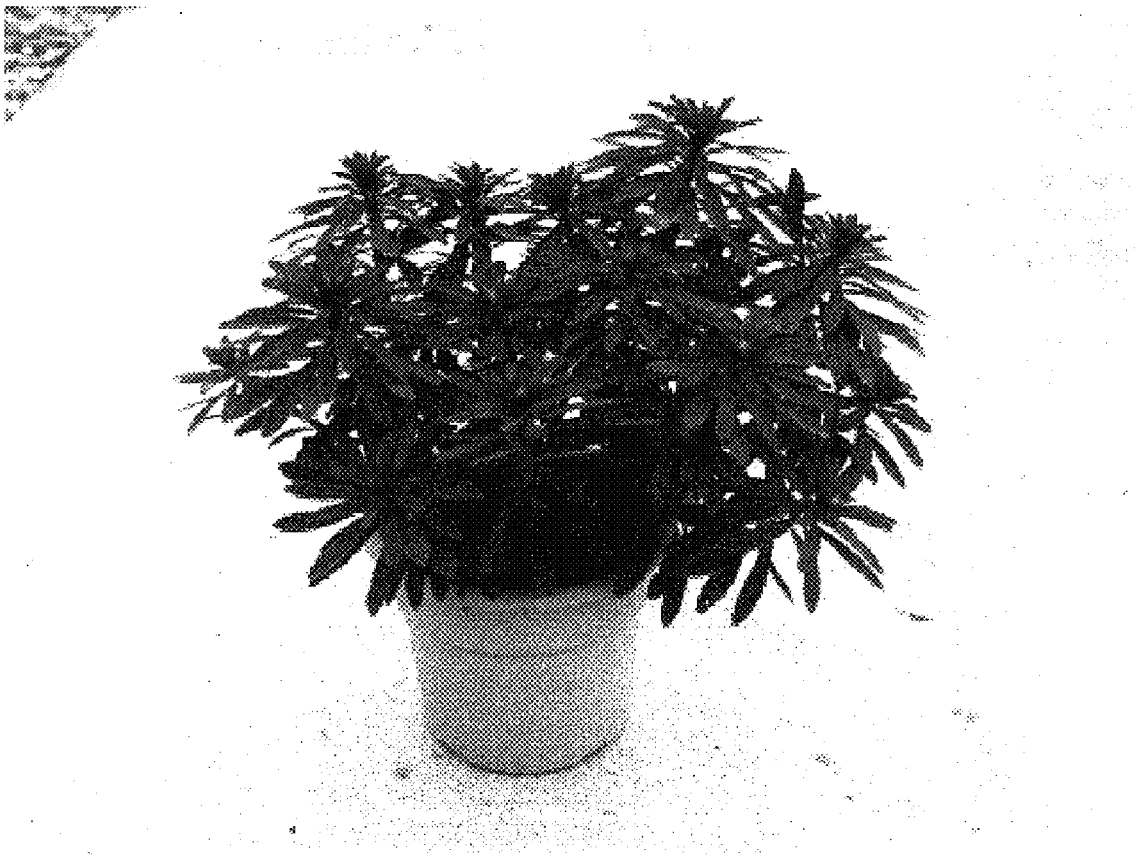
FIG. 1, FIG. 2, and FIG. 3, illustrate the overall appearance of the new *Euphorbia* cultivar 'WALEUPHRUD' showing the colors as true as it is reasonably possible to obtain in colored reproductions of this type. Colors in the drawings may differ from the color values cited in the detailed botanical description, which accurately describe the actual colors of the new variety 'WALEUPHRUD'.
Figure 2:
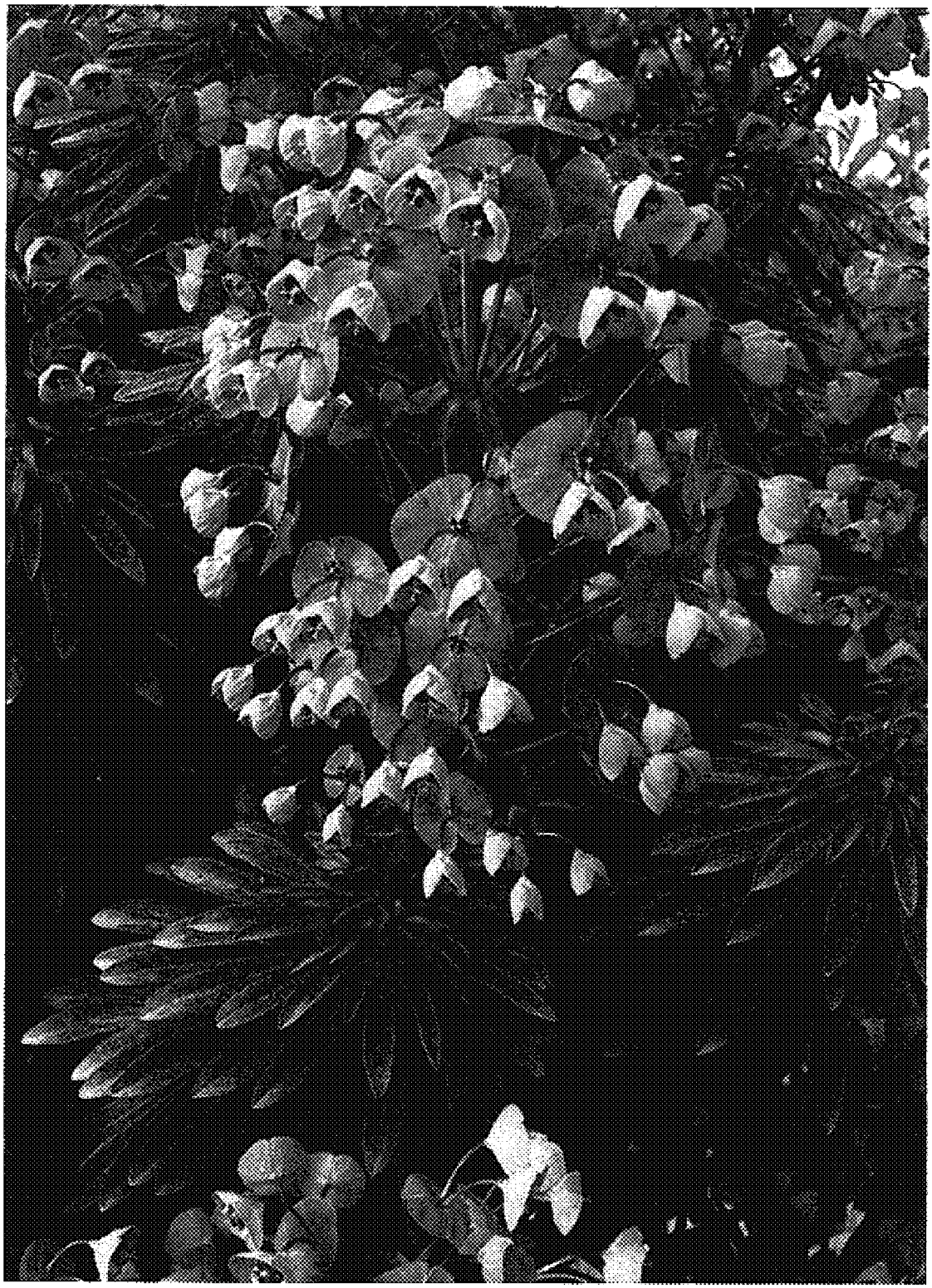
Figure 3:
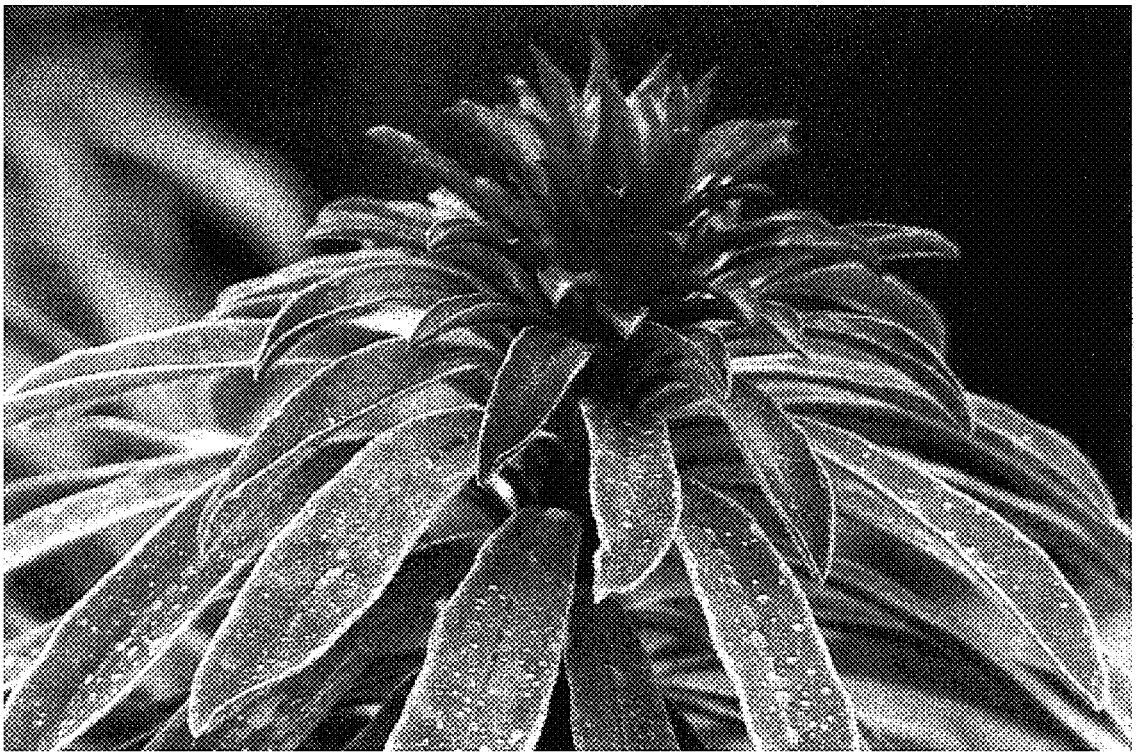

The following is a detailed botanical description of the new *Euphorbia×martinii* cultivar 'WALEUPHRUD'. Observations, measurements, values and comparisons were collected in Arroyo Grande, Calif. from 1- liter container plants that were 12-months-old at the time and grown out-of-doors in full sun. Color determinations are made in accordance with the 2001 edition of The Royal Horticultural Society Colour Chart of London, England, except where general color terms of ordinary dictionary significance are used. The growing requirements of the new variety are similar to the species.

Botanical classification: *Euphorbia×martinii* 'WALEUPHRUD'.

Genus: *Euphorbia.*

Species: *×martinii.*

Denomination: WALEUPHRUD.

Common name: Spurge.

Commercial classification: Ornamental sub-shrub.

Parentage: *Euphorbia×martinii* 'WALEUPHRUD' was discovered as a naturally occurring single branch sport on an individual *Euphorbia×martinii* (unpatented) that was growing in a commercial crop of *Euphorbia×martinii.*

Asexual propagation method: Vegetative cuttings.

Rooting habit: Fine.

Time to develop roots: 2 weeks are needed for roots to develop on an initial cutting.

Temperature recommended to develop roots: 18° Centigrade.

Crop time: A range of 8 to 12-months are needed to produce a finished 1-liter container from a rooted cutting.

Growth habit: Compact habit.

Plant shape: Closest to oblate.

Plant use: Suitable for use in container, rock garden, and as a groundcover for the landscape.

Plant type: Perennial.

Plant vigor: Moderate vigor.

Dimensions of plant at maturity: 60 cm. in height and 60 cm. in width at maturity.

Dimensions of plant in 1-liter container: 34 cm. in height and 37 cm. in width in a 1- liter container.

Cultural requirements: Sun or partial shade, moderate water, and well-draining soil.

Diseases and pests: Can be affected by *fusarium, phytophthora,* and red spider.

Hardiness: Hardy from USDA Zone 7 to USDA Zone 10.

Special considerations: Hazardous. All parts exude a white milky substance when bruised that can be toxic and may elicit dermal irritation.

Stem:

*Branching habit.*—Central trunk with laterally branching stems.

*Trunk dimensions.*—2.50 cm. in diameter and 1.50 cm. in height.

*Trunk shape.*—Columnar.

*Trunk surface.*—Pubescent surface.

*Trunk color.*—Colors 179A and 144A are individually present on an individual trunk.

*Quantity of lateral stems.*—Quantity of lateral stems range from 13 to 15 per individual 1-liter container plant.

*Lateral stem color.*—Colors 179A and 145A are individually present on an individual lateral stem.

*Lateral stem shape.*—Columnar.

*Lateral stem length.*—An individual lateral stem is an average of 29 cm. in length on an individual container plant.

*Lateral stem diameter.*—An individual lateral stem is an average of 0.50 cm. in diameter on an individual container plant.

*Lateral stem surface.*—Pubescent.

Foliage (bract-leaf refers to leaf appendages on winter shoots):

*Type.*—Evergreen.

*Leaf arrangement.*—Spiral arrangement.

*Internode length.*—Internodes are 0.50 cm. in length.

*Leaf division.*—Simple.

*Leaf shape.*—Oblanceolate with slightly involute edges.

*Leaf length.*—An individual leaf averages 4.25 cm. in length on an individual container plant.

*Leaf width.*—An individual leaf averages 1 cm. in width on an individual container plant.

*Leaf apex.*—Acute.

*Leaf base.*—Attenuate.

*Quantity of leaves.*—An average quantity of 40–60 leaves per stem.

*Leaf venation pattern (abaxial and adaxial surfaces).*—Pinnate with only the mid-vein prominent.

*Vein color (abaxial surface).*—185C.

*Vein color (adaxial surface).*—185C.

*Margin.*—Entire.

*Leaf surface (abaxial surface).*—Pubescent.

*Leaf surface (adaxial surface).*—Pubescent.

*Leaf appearance (adaxial and abaxial surfaces).*—Matte.

*Leaf attachment.*—Sessile.

*Leaf color (adaxial surface).*—A combination of colors 191A, 191B, 189A, and N189A are present on the foliage of an individual plant.

*Leaf color (abaxial surface).*—A combination of colors 191A, 191B, 189A, and N189A are present on the foliage of an individual plant.

*Bract-leaf color (adaxial surface).*—Colors 186A and 189C are individually present on an individual bract-leaf.

*Bract-leaf color (abaxial surface).*—Colors 186A, 161C, and 189C are individually present on an individual bract-leaf.

*Bract-leaf surfaces (abaxial and adaxial surfaces).*—Lightly puberulent.

*Bract-leaf appearance (abaxial and adaxial surfaces).*—Matte.

*Bract-leaf arrangement.*—Whorled.

*Bract-leaf margin.*—Entire.
*Bract-leaf attachment.*—Sessile.
*Bract-leaf shape.*—Closest to oblanceolate with involute edges.
*Bract-leaf apex.*—Acute.
*Bract-leaf base.*—Attenuate.
*Bract-leaf width.*—An individual bract-leaf ranges from 0.50 cm. to 1 cm. in width on an individual plant.
*Bract-leaf length.*—An individual bract-leaf ranges from 1.75 cm. to 2.25 cm. in length on an individual plant.
*Foliage fragrance.*—Slight medicinal scent observed.

Flower:
*Type of inflorescence.*—Cyathium.
*Cyathium shape.*—Cupulate.
*Bloom seasons.*—Spring and summer.
*Bud shape.*—Oval in shape.
*Bud dimensions.*—4 mm. in length and 3 mm. in diameter.
*Bud surface.*—Glabrous.
*Bud color.*—N144A.
*Bud apex.*—Rounded.
*Dimensions of individual cyathium.*—An individual cyathium is an average of 0.50 cm. in diameter and 0.55 cm. in depth on an individual plant.
*Cyathium color.*—A combination of colors 144A and 144B are present on an individual cyathium.
*Cyathia arrangement.*—Whorled.
*Quantity of cyathia per peduncle.*—Quantity ranges from 56–65 cyathia per individual peduncle.
*Quantity of cyyathia per pedicel.*—An average of 2 cyathia per individual pedicel.
*Aspect.*—Facing outward and downward.
*Petals.*—Apetalous.
*Sepals.*—Asepalous.
*True perianth.*—Absent.
*Penducle length.*—An individual peduncle is an average of 27 cm. in length on an individual container plant.
*Peduncle diameter.*—An individual peduncle is an average of 0.40 cm. in diameter on an individual container plant.
*Peduncle shape.*—Columnar in shape.
*Peduncle color.*—183A.
*Peduncle appearance.*—Semi-glossy.
*Peduncle surface.*—Puberulent.
*Pedicel length.*—An individual pedicel ranges from 0.50 cm. to 3.50 cm. in length on an individual container plant.
*Pedicel diameter.*—An individual pedicel ranges from 0.75 mm. to 2 mm. in diameter on an individual container plant.
*Pedicel shape.*—Cylindrical in shape.
*Pedicel color.*—Colors 144A and 178A are individually present on an individual pedicel.
*Pedicel surface.*—Puberulent.
*Floral leaf quantity.*—An average of 2 floral leaves per individual pedicel.
*Floral leaves fused or unfused.*—Floral leaves are basally fused.
*Floral leaf attachment.*—Connate perfoliate.
*Floral leaf color* (*abaxial surface.*).—147B.
*Floral leaf color* (*adaxial surface*).—147B.
*Floral leaf margin.*—Entire.
*Floral leaf shape shape.*—Reniform.
*Floral leaf apex.*—Obtuse apex.
*Floral leaf base.*—Closest to truncate.
*Floral leaf dimensions.*—Average dimensions of an individual floral leaf are 0.75 cm. in length and 1 cm. in width.
*Floral leaf surfaces* (*adaxial and abaxial surfaces*).—Glabrous.
*Lastingness of cyathium on plant.*—The range of time that an individual cyathium lasts on an individual container plant is 10 to 15 days.
*Lastingness of cyathium* (*when removed from plant*).—An individual cyathium lasts an average of 24 hours when removed from a plant.
*Cyathium fragrance.*—Slight medicinal scent observed.

Reproductive organs:
*Stamen color.*—144C.
*Number of stamens.*—Four in number.
*Stamen dimensions.*—1 mm. in length and 0.25 mm. in diameter.
*Anther dimensions.*—0.50 mm. in length and 0.50 mm. in width.
*Anther shape.*—Round.
*Anther color.*—144C.
*Pollen.*—None observed.
*Nectaries.*—4 in number.
*Nectary surface.*—Glossy.
*Nectary color.*—Colors 185A and 162A are individually present on an individual nectary.
*Nectary dimensions.*—2.25 mm. in width and 1.20 mm. in length.
*Nectary shape.*—Cresent-shaped.
*Pistil.*—One in number.
*Pistil dimensions.*—Pistil is 5 mm in length and 0.75 mm in diameter.
*Pistil color.*—N144B.
*Style number.*—Three lobes that are basally fused.
*Style dimensions.*—2 mm. in length and 0.50 mm in width.
*Style color.*—N144B.
*Stigma color.*—N144B.
*Stigma number.*—3 individual bifid stigmas.
*Stigma dimensions.*—0.50 mm. in length and 0.10 mm in width.
*Ovary shape.*—Globular in shape.
*Ovary surface.*—Pubescent.
*Ovary dimensions.*—1.75 mm. in width and 1.75 mm. in height.
*Ovary color.*—144A.
*Ovary position.*—Superior.

Seed: No seed has been observed to date.

It is claimed:

1. A new and distinct cultivar of *Euphorbia* plant named 'WALEUPHRUD' as described and illustrated herein.

* * * * *